US009486548B2

United States Patent
Aurongzeb et al.

(10) Patent No.: US 9,486,548 B2
(45) Date of Patent: Nov. 8, 2016

(54) SYSTEM AND METHOD FOR REDUCING TOUCH INDUCED CONTAMINATION

(71) Applicant: Dell Products, LP, Round Rock, TX (US)

(72) Inventors: Deeder M. Aurongzeb, Round Rock, TX (US); Kenneth C. Musgrave, Austin, TX (US)

(73) Assignee: Dell Products, LP, Round Rock, TX (US)

( * ) Notice: Subject to any disclaimer, the term of this patent is extended or adjusted under 35 U.S.C. 154(b) by 231 days.

(21) Appl. No.: 13/857,878

(22) Filed: Apr. 5, 2013

(65) Prior Publication Data

US 2014/0300581 A1 Oct. 9, 2014

(51) Int. Cl.
*A61L 2/10* (2006.01)
*G06F 1/16* (2006.01)

(52) U.S. Cl.
CPC .............. *A61L 2/10* (2013.01); *G06F 1/1601* (2013.01); *A61L 2202/16* (2013.01); *G06F 1/1677* (2013.01)

(58) Field of Classification Search
CPC .. G06F 1/1677; G06F 1/1601; G06F 1/1675; G06F 1/1679; A61L 2/10
See application file for complete search history.

(56) References Cited

U.S. PATENT DOCUMENTS

| | | | |
|---|---|---|---|
| 5,920,075 A * | 7/1999 | Whitehead | 250/492.1 |
| 8,264,470 B2 * | 9/2012 | Sakurai | 345/173 |
| 8,289,115 B2 * | 10/2012 | Cretella et al. | 335/219 |
| 8,321,709 B2 * | 11/2012 | Jin et al. | 713/323 |
| 8,325,141 B2 | 12/2012 | Marsden | |
| 8,339,373 B2 | 12/2012 | Chang | |
| 2006/0188389 A1 * | 8/2006 | Levy | 422/24 |
| 2007/0195550 A1 * | 8/2007 | Tsai | 362/600 |
| 2010/0045623 A1 * | 2/2010 | Sakurai | 345/173 |
| 2010/0127189 A1 | 5/2010 | Boyarsky et al. | |
| 2011/0256019 A1 | 10/2011 | Gruen et al. | |
| 2012/0072167 A1 * | 3/2012 | Cretella et al. | 702/150 |
| 2012/0106078 A1 * | 5/2012 | Probst | G06F 1/1616 361/679.56 |
| 2014/0183377 A1 * | 7/2014 | Bettles et al. | 250/455.11 |

\* cited by examiner

*Primary Examiner* — Quan-Zhen Wang
*Assistant Examiner* — Xuemei Zheng
(74) *Attorney, Agent, or Firm* — Larson Newman, LLP (57) ABSTRACT

A contamination control system of an electronic device includes a touch-based surface, an ultraviolet (UV) light source operable to shine on the touch-based surface, a detection module, and a control module. The detection module detects a first event indicating that a user has interacted with the touch-based surface, sends a first indication based upon the first event, detects a second event indicating that a user is done interacting with the touch-based surface, and sends a second indication based upon the second event. The control module receives the first indication and the second indication from the detection module and turns on the UV light source to decontaminate the touch-based surface in response to the first indication and the second indication.

15 Claims, 5 Drawing Sheets

SYSTEM AND METHOD FOR REDUCING TOUCH INDUCED CONTAMINATION

FIELD OF THE DISCLOSURE

This disclosure relates generally information handling systems, and more particularly relates to reducing touch induced contamination in an information handling system.

BACKGROUND

As the value and use of information continues to increase, individuals and businesses seek additional ways to process and store information. One option is an information handling system. An information handling system generally processes, compiles, stores, and/or communicates information or data for business, personal, or other purposes. Because technology and information handling needs and requirements may vary between different applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software resources that may be configured to process, store, and communicate information and may include one or more computer systems, data storage systems, and networking systems. Touch-based devices and public displays are increasingly interacted with by multiple users.

BRIEF DESCRIPTION OF THE DRAWINGS

It will be appreciated that for simplicity and clarity of illustration, elements illustrated in the Figures have not necessarily been drawn to scale. For example, the dimensions of some of the elements are exaggerated relative to other elements. Embodiments incorporating teachings of the present disclosure are shown and described with respect to the drawings presented herein, in which.

The use of the same reference symbols in different drawings indicates similar or identical items.

DETAILED DESCRIPTION OF DRAWINGS

The following description in combination with the Figures is provided to assist in understanding the teachings disclosed herein. The following discussion will focus on specific implementations and embodiments of the teachings. This focus is provided to assist in describing the teachings, and should not be interpreted as a limitation on the scope or applicability of the teachings. However, other teachings can certainly be used in this application. The teachings can also be used in other applications, and with several different types of architectures, such as distributed computing architectures, client/server architectures, or middleware server architectures and associated resources.

Figure 1:
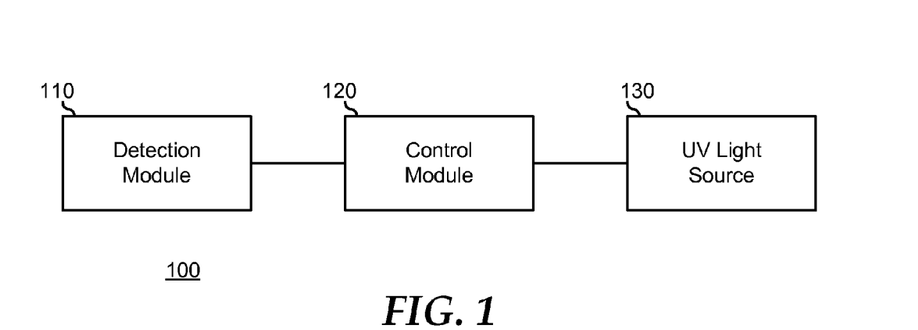
FIG. 1 is a block diagram illustrating a contamination control system according to an embodiment of the present disclosure.

FIG. 1 illustrates an embodiment of a contamination control system 100, including a detection module 110, a control module 120, and an ultra-violet (UV) light source. UV germicidal irradiation (UVGI) is a disinfection method that uses UV light to kill microorganism. Contamination control system 100 uses UV light source 130 to irradiate the surface of an electronic device that includes the contamination control system. For example, contamination control system 100 can be included in an electronic device that includes a touch screen panel, such as a laptop computer, a smart phone, a tablet device, a public display or terminal device such as an information kiosk or an automated teller machine (ATM), or another touch screen panel device. Contamination control system 100 can also be included in an electronic device that includes a keypad, a keypad, or another touch-based user interface device.

Detection module 110 represents one or more sensors or operating conditions of the electronic device that are used to indicate that no user is in the vicinity of the electronic device, or that the electronic device is otherwise disposed such that it is safe to operate UV light source 130. In operation, detection module 110 receives inputs from the one or more sensors and indications from the one or more operating conditions that are interpreted by the detection module as indicating that it is safe to operate UV light source 130. An example of a sensor that can provide an input to detection module 110 includes a motion sensor, such as a camera device, a light sensor, a position sensor, an accelerometer, another sensor device, or a combination thereof. An example of an operating condition that can indicate that it is safe to operate UV light source includes a state of the electronic device, such as a basic input/output system (BIOS) power state indication, a timer, a time of day, or day of the week indication, another operating condition, or a combination thereof. Here, a particular use case can include receiving a combination of sensor inputs and condition indications that demonstrate that a user is not present at the electronic device, that the device is located in a particular business that is closed during certain hours of the day and that the current time indicates that the business is presently closed, that a user of the electronic device has placed the device in a condition or state that indicates that the user wishes to decontaminate the device, or another use case, as needed or desired.

When detection module 110 determines that it is safe to operate UV light source 130, the detection module provides an indication to control module 120. In response, control module 120 turns on UV light source 130. In a particular embodiment, control module 120 operates to time the duration that UV light source 130 is turned on. Here, a particular duration of UVGI can be sufficient to disinfect the surface of the electronic device. As such, by maintaining the duration that UV light source 130 is turned on to at or near the particular duration, control module 120 operates to disinfect the surface while limiting the amount of power used to perform the disinfection. This may be a useful consideration where the electronic device is a battery operated device, such as a laptop computer, a smart phone, a tablet device, or another mobile electronic device. In another embodiment, control module 120 operates to track an amount of use that the surface of the electronic device is utilized, and to cycle the operation of UV light source 130 when the amount of use exceeds a threshold. In a similar embodiment, control module 120 operates to track when different users have used the surface of the electronic device, and to cycle the operation of UV light source 130 after each user has used the electronic device. Here, where the electronic device represents a public display or terminal device, control module 120 can operate to cycle UV light source 130 after each user has used the electronic device.

UV light source 130 represents one or more elements that are configured to emit UV light, such as UV light emitting diodes (LEDs). In a particular embodiment, UV light source 130 includes elements that are integrated with other portions of the electronic device, such as with the backlight elements of a liquid crystal display (LCD) touch panel. In another embodiment, UV light source 130 includes discrete elements that are situated to shine on the surface of the electronic device that is to be decontaminated.

Figure 2:
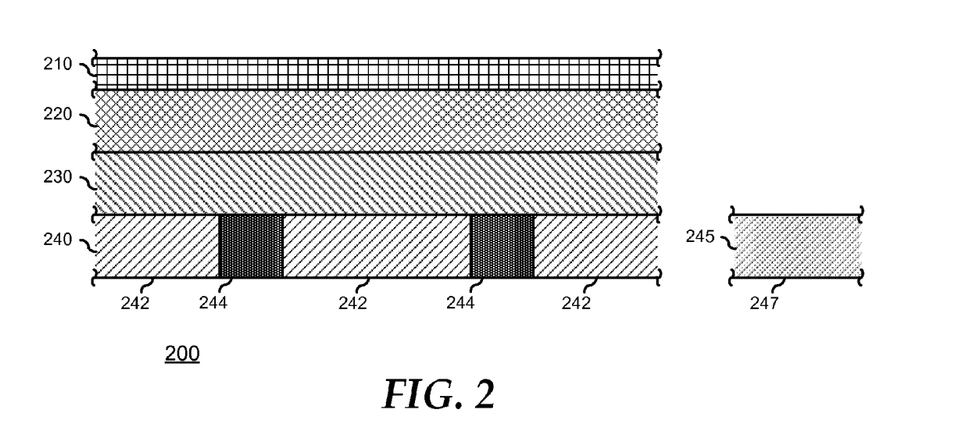
FIG. 2 is an illustration of a liquid crystal display touch panel according to an embodiment of the present disclosure.

FIG. 2 illustrates an embodiment of an LCD touch panel 200 of an electronic device, including a touch screen 210, a touch detector 220, an liquid crystal array 230, and a backlight layer 240. Liquid crystal array 230 is coupled to a display adapter of the electronic device to provide a displayed image as needed or required by the electronic device. Backlight layer 240 operates in conjunction with liquid crystal array 230 to provide brightness and contrast to the displayed image provided by liquid crystal array 240. Touch detector 220 is coupled to an input adapter to provide a user with a way to interact with the electronic device, and touch screen 210 is a cover for LCD touch panel to which the user provides the touch inputs. Multiple users can interact with LCD touch panel 200, such that the surface of touch screen 210 can retain contaminants from one user, and pass them to a next user. To mitigate the problem of decontaminating the surface of touch screen 210, back panel 240 includes UV light sources 244, interspersed with backlight sources 242, that can be turned on to provide UVGI to the surface of touch screen 210. As such, UV light sources 244 can operate similarly to UV light source 130, and the electronic device that includes LCD touch panel 200 can also include a contamination control system similar to contamination control system 100 and that can control the operation of UV light sources 244 to decontaminate the surface of touch panel 210. In another embodiment, backlight layer 240 is replaced with a backlight layer 245 that includes backlight source 247 similar to backlight source 242. Here, backlight source 247 operates to provide UV light as a portion of the light spectrum that is provided by the backlight source. LCD touch panel 200 is adapted to provide UVGI for electronic devices that include flat panel displays and, as described below, for keyboard surfaces of laptop devices.

Figure 3:
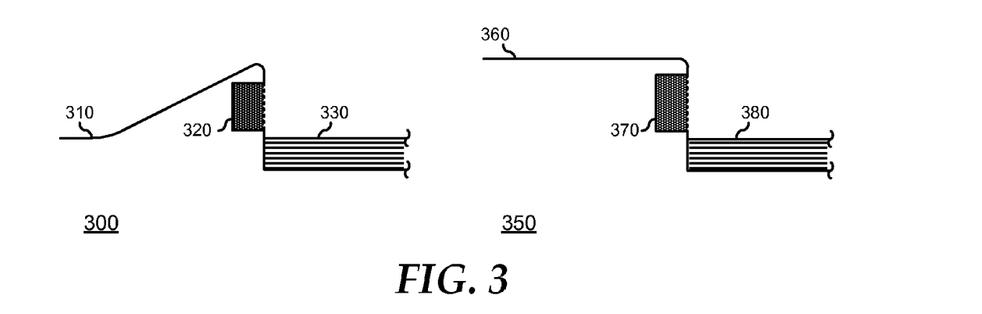
FIG. 3 is a view of ultraviolet decontamination arrangements according to embodiments of the present disclosure.

FIG. 3 illustrates embodiments of UV decontamination arrangements 300 and 350. UV decontamination arrangement 300 includes a case 310, a UV light source 320, and a surface 330. In this embodiment, case 310 is a case for an electronic device that is configured with a raised profile to house UV light source 320 such that the UV light source shines on surface 330 when the UV light source is turned on. Surface 330 represents a surface of the electronic device that provides for user inputs to be provided to the electronic device. For example, surface 330 can include an LCD touch panel similar to LCD touch panel 200, a keyboard, a key pad, a fingerprint scanner, another surface, or a combination thereof. Here, because case 310 is configured to house UV light source 320 to be able to shine on surface 330, the surface can be decontaminated when the UV light source is turned on. UV decontamination arrangement 350 includes a case 360, a UV light source 370, and a surface 380. In this embodiment, case 360 is a case for an electronic device that is configured with a bezel that houses UV light source 370 such that the UV light source shines on surface 380 when the UV light source is turned on. Surface 380 is similar to surface 330, and UV decontamination arrangement 350 operates similarly to UV decontamination arrangement 300. However, UV decontamination arrangement 350 provides the similar functionality without the raised profile of UV decontamination arrangement 300. UV decontamination arrangements 300 and 350 are adapted to provide UVGI for electronic devices that include flat panel displays, keyboards, or other user interfaces.

Figure 4:
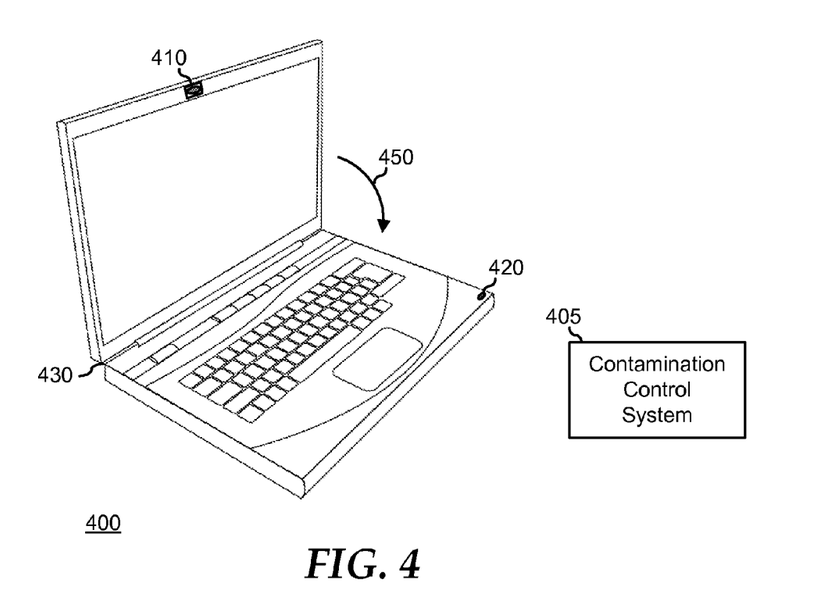
FIG. 4 is a view of a laptop computer according to an embodiment of the present disclosure.

FIG. 4 illustrates an embodiment of a laptop computer 400 including a contamination control system 405 similar to contamination control system 100, a camera 410, a light sensor 420, and a lid position sensor 430. In addition, laptop computer 400 includes one or more of an LCD touch panel similar to LCD touch panel 200, and UV decontamination arrangements similar to decontamination arrangements 300 and 350. In a particular embodiment, one or more of camera 410, light sensor 420, and lid position sensor 430 are used to indicate that no user is in the vicinity of laptop computer 400, or that the electronic device is otherwise disposed such that it is safe to operate the UV light source associated with the LCD touch panel or the decontamination arrangement. In operation, a detection module similar to detection module 110 receives inputs from one or more of camera 410, light sensor 420, and lid position sensor 430 indicating that it is safe to operate the UV light source. For example, camera 410 can operate as a motion sensor to detect the presence of a user, and when no user is detected, contamination control system 405 can operate the UV light source to decontaminate the LCD touch panel, and the keyboard. In another embodiment, when the lid of laptop computer 400 is closed 450, light sensor 420 can detect the lid closure, lid position sensor 430 can detect the lid closure, or camera 410 can detect the lid closure. In any case, when the lid is closed 450, contamination control system 405 can operate the UV light source to decontaminate the LCD touch panel, and the keyboard. In a particular embodiment, where laptop computer 400 includes an LCD touch panel similar to LCD touch panel 200, turning on the UV light source in the LCD touch panel while the lid is closed operates to decontaminate both the surface of the LCD touch panel, and the keyboard because the UV light source shines on both the surface of the LCD touch panel and the keyboard.

Figure 5:
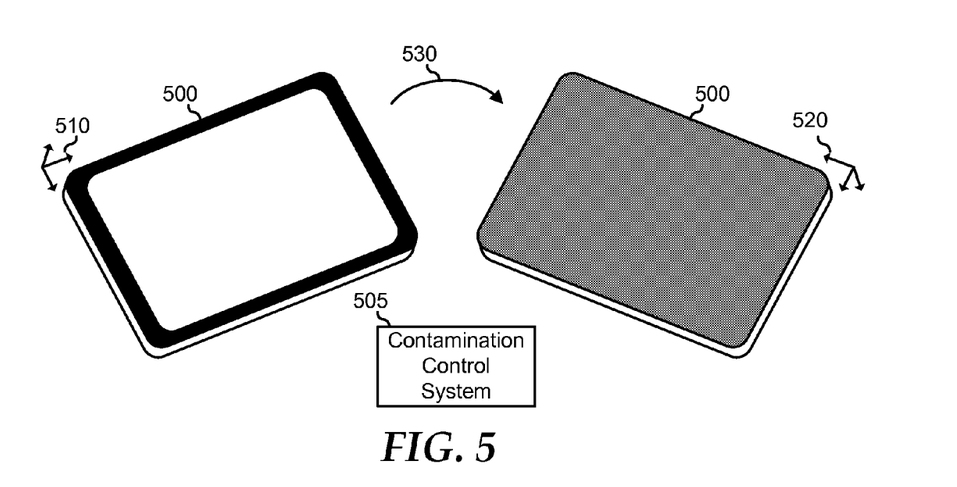
FIG. 5 is a view of a tablet device according to an embodiment of the present disclosure.

FIG. 5 illustrates an embodiment of a tablet device 500 that includes a contamination control system 505 similar to contamination control system 100, a position sensor 510, and an LCD touch panel similar to LCD touch panel 200. Here, when tablet device 500 is turned face-down 530, that is, when the surface of the LCD touch panel is facing downward, contamination control system 505 can determine that it is safe to turn on the UV light source to decontaminate the surface of the LCD touch panel.

Figure 6:
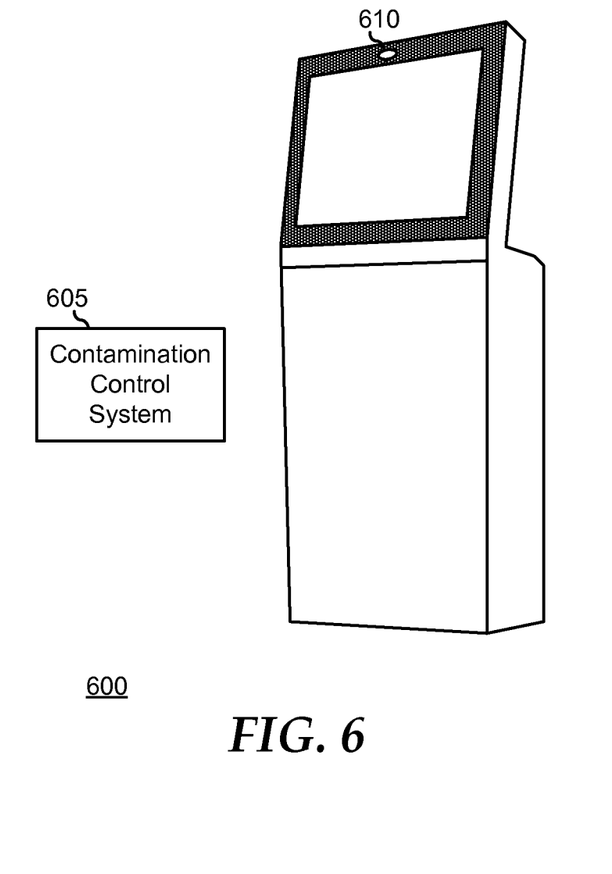
FIG. 6 is a view of an information kiosk according to an embodiment of the present disclosure.

FIG. 6 illustrates an embodiment of an information kiosk 600 that includes a contamination control system 605 similar to contamination control system 100, a camera 610, and an LCD touch panel similar to LCD touch panel 200. Here, when camera 510 detects that no user is using information kiosk 600, contamination control system 605 can determine that it is safe to turn on the UV light source to decontaminate the surface of the LCD touch panel.

Figure 7:
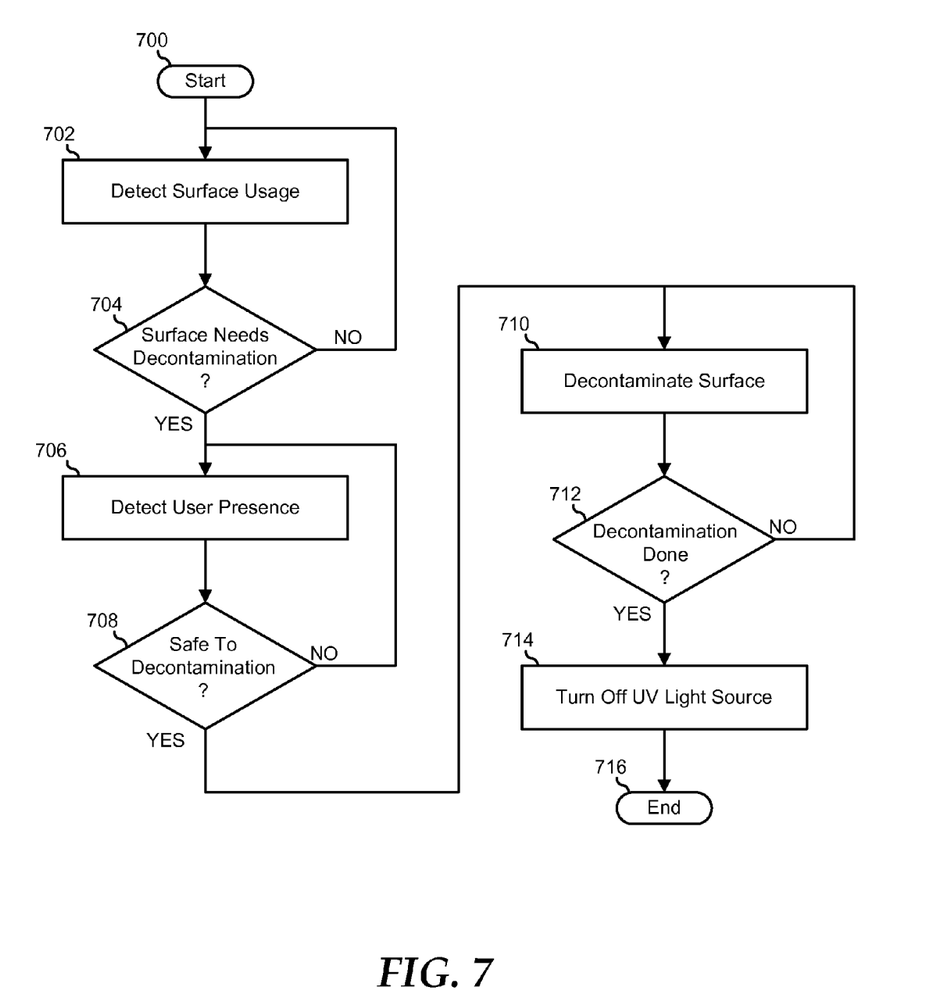
FIG. 7 is a flow chart illustrating a method for reducing touch induced contamination in an information handling system according to an embodiment of the present disclosure.

FIG. 7 illustrates an embodiment of a method for to reducing touch induced contamination in an information handling system starting at block 700. The usage of the surface of an electronic device is detected in block 702. For example, a contamination control system can determine that a user has interacted with a touch surface of an electronic device, that the user has interacted with the touch surface for more than a predetermined amount of time, or otherwise has interacted with the touch surface. A decision is made as to whether or not the surface needs to be decontaminated in decision block 704. If not, the "NO" branch of decision block 704 is taken and the method returns to block 702 where the usage of the surface of the electronic device is detected. If surface needs to be decontaminated, the "YES" branch of decision block 704 is taken and the presence of a user is detected in block 706. For example, the contamination control system can determine that a user of the electronic device is not in the proximity of the electronic device, that the electronic device is closed or turned face down, that the user of an information kiosk has left the kiosk, or the like.

A decision is made as to whether or not it is safe to decontaminate the surface in decision block 708. If not, the "NO" branch of decision block 708 is taken and the method returns to block 706 where the presence of a user is detected. If not it is safe to decontaminate the surface, the "YES" branch of decision block 708 is taken and the surface is decontaminated in block 710. For example, a UV light source can be turned on to decontaminate the surface. A decision is made as to whether or not the surface is decontaminated in decision block 712. If not, the "NO" branch of decision block 712 is taken, and the method returns to block 710 where the surface decontamination is continued. If the surface is decontaminated, the "YES" branch of decision block 712 is taken, the UV light source is turned off in block 714, and the method ends in block 716.

Figure 8:
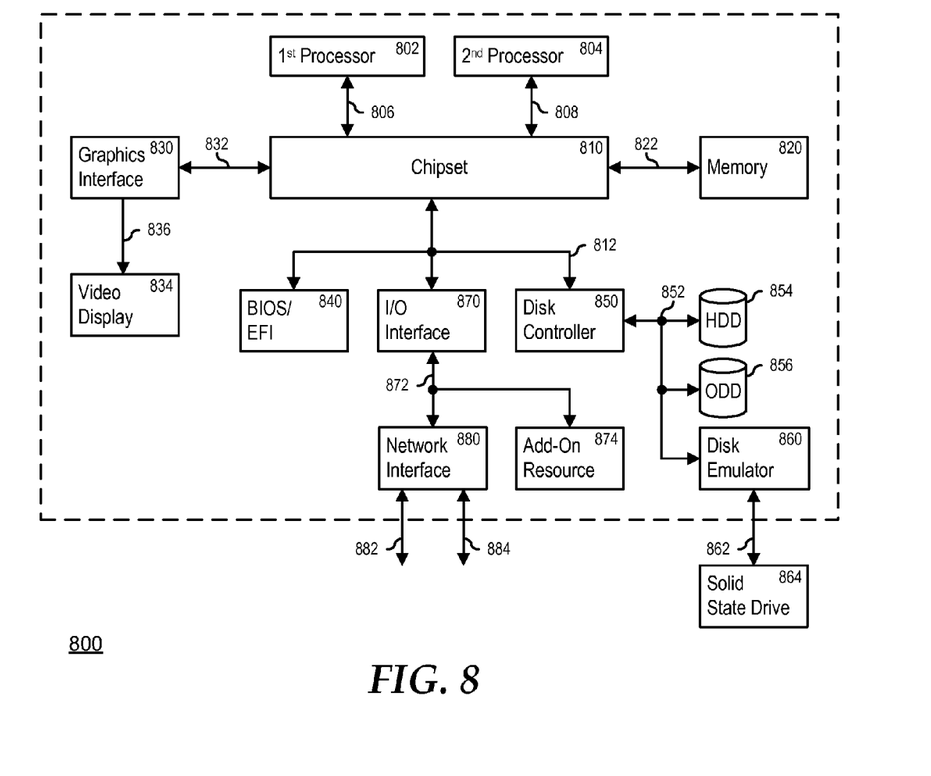
FIG. 8 is a block diagram illustrating a generalized information handling system according to an embodiment of the present disclosure.

FIG. 8 illustrates a generalized embodiment of information handling system 800. For purpose of this disclosure information handling system 800 can include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, entertainment, or other purposes. For example, information handling system 100 can be a personal computer, a laptop computer, a smart phone, a tablet device or other consumer electronic device, a network server, a network storage device, a switch router or other network communication device, or any other suitable device and may vary in size, shape, performance, functionality, and price. Further, information handling system 100 can include processing resources for executing machine-executable code, such as a central processing unit (CPU), a programmable logic array (PLA), an embedded device such as a System-on-a-Chip (SoC), or other control logic hardware. Information handling system 800 can also include one or more computer-readable medium for storing machine-executable code, such as software or data. Additional components of information handling system 800 can include one or more storage devices that can store machine-executable code, one or more communications ports for communicating with external devices, and various input and output (I/O) devices, such as a keyboard, a mouse, and a video display. Information handling system 800 can also include one or more buses operable to transmit information between the various hardware components.

Information handling system 800 can include devices or modules that embody one or more of the devices or modules described above, and operates to perform one or more of the methods described above. Information handling system 800 includes a processors 802 and 804, a chipset 810, a memory 820, a graphics interface 830, include a basic input and output system/extensible firmware interface (BIOS/EFI) module 840, a disk controller 850, a disk emulator 860, an input/output (I/O) interface 870, and a network interface 880. Processor 802 is connected to chipset 810 via processor interface 806, and processor 804 is connected to the chipset via processor interface 808. Memory 820 is connected to chipset 810 via a memory bus 822. Graphics interface 830 is connected to chipset 810 via a graphics interface 832, and provides a video display output 836 to a video display 834. In a particular embodiment, information handling system 800 includes separate memories that are dedicated to each of processors 802 and 804 via separate memory interfaces. An example of memory 820 includes random access memory (RAM) such as static RAM (SRAM), dynamic RAM (DRAM), non-volatile RAM (NV-RAM), or the like, read only memory (ROM), another type of memory, or a combination thereof.

BIOS/EFI module 840, disk controller 850, and I/O interface 870 are connected to chipset 810 via an I/O channel 812. An example of I/O channel 812 includes a Peripheral Component Interconnect (PCI) interface, a PCI-Extended (PCI-X) interface, a high-speed PCI-Express (PCIe) interface, another industry standard or proprietary communication interface, or a combination thereof. Chipset 810 can also include one or more other I/O interfaces, including an Industry Standard Architecture (ISA) interface, a Small Computer Serial Interface (SCSI) interface, an Inter-Integrated Circuit ($I^2C$) interface, a System Packet Interface (SPI), a Universal Serial Bus (USB), another interface, or a combination thereof. BIOS/EFI module 840 includes BIOS/EFI code operable to detect resources within information handling system 800, to provide drivers for the resources, initialize the resources, and access the resources. BIOS/EFI module 840 includes code that operates to detect resources within information handling system 800, to provide drivers for the resources, to initialize the resources, and to access the resources.

Disk controller 850 includes a disk interface 852 that connects the disc controller to a hard disk drive (HDD) 854, to an optical disk drive (ODD) 856, and to disk emulator 860. An example of disk interface 852 includes an Integrated Drive Electronics (IDE) interface, an Advanced Technology Attachment (ATA) such as a parallel ATA (PATA) interface or a serial ATA (SATA) interface, a SCSI interface, a USB interface, a proprietary interface, or a combination thereof. Disk emulator 860 permits a solid-state drive 864 to be coupled to information handling system 800 via an external interface 862. An example of external interface 862 includes a USB interface, an IEEE 1394 (Firewire) interface, a proprietary interface, or a combination thereof. Alternatively, solid-state drive 864 can be disposed within information handling system 800.

I/O interface 870 includes a peripheral interface 872 that connects the I/O interface to an add-on resource 874 and to network interface 880. Peripheral interface 872 can be the same type of interface as I/O channel 812, or can be a different type of interface. As such, I/O interface 870 extends the capacity of I/O channel 812 when peripheral interface 872 and the I/O channel are of the same type, and the I/O interface translates information from a format suitable to the I/O channel to a format suitable to the peripheral channel 872 when they are of a different type. Add-on resource 874 can include a data storage system, an additional graphics interface, a network interface card (NIC), a sound/video processing card, another add-on resource, or a combination thereof. Add-on resource 874 can be on a main circuit board, on separate circuit board or add-in card disposed within information handling system 800, a device that is external to the information handling system, or a combination thereof.

Network interface 880 represents a NIC disposed within information handling system 800, on a main circuit board of the information handling system, integrated onto another component such as chipset 810, in another suitable location, or a combination thereof. Network interface device 880 includes network channels 882 and 884 that provide interfaces to devices that are external to information handling system 800. In a particular embodiment, network channels 882 and 884 are of a different type than peripheral channel 872 and network interface 880 translates information from a format suitable to the peripheral channel to a format suitable to external devices. An example of network channels 882 and 884 includes InfiniBand channels, Fibre Channel channels, Gigabit Ethernet channels, proprietary channel architectures, or a combination thereof. Network channels 882 and 884 can be coupled to external network resources (not illustrated). The network resource can include another information handling system, a data storage system, another network, a grid management system, another suitable resource, or a combination thereof.

Although only a few exemplary embodiments have been described in detail herein, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

The above-disclosed subject matter is to be considered illustrative, and not restrictive, and the appended claims are intended to cover any and all such modifications, enhancements, and other embodiments that fall within the scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A contamination control system of an electronic device, the contamination control system comprising:
 a touch-based surface;
 an ultraviolet (UV) light source operable to shine on the touch-based surface;
 a detection module operable to:
  detect a first event indicating that a user has provided a touch-based input to the touch-based surface;
  send a first indication based upon the first event;
  detect a second event indicating that the user has moved away from the touch-based surface;
  send a second indication based upon the second event;
  detect a duration for the first event; and
  send a third indication when the duration for the first event exceeds a threshold; and
 a control module operable to:
  receive the first indication, the second indication, and the third indication from the detection module;
  determine that it is safe to turn on the UV light source to decontaminate the touch-based surface in response to the first indication, the second indication, and the third indication; and
  turn on the UV light source to decontaminate the touch-based surface in response to determining that it is safe to turn on the UV light source;
 wherein the UV light source comprises a UV light emitting diode (LED) configured within a raised profile of a case of the electronic device, the LED being disposed to shine on the touch-based surface.

2. The contamination control system of claim 1, wherein: the UV light source comprises a liquid crystal display (LCD) touch panel.

3. The contamination control system of claim 2, wherein: the electronic device comprises a laptop computer; the touch-based surface comprises a touch surface of the LCD touch panel and a keyboard; the second event includes closing a lid of the laptop computer; and decontaminating the touch-based surface comprises decontaminating the touch surface and the keyboard.

4. The contamination control system of claim 3, wherein the detection module is operable to detect that the lid is closed based upon a camera of the laptop device.

5. The contamination control system of claim 3, wherein the detection module is operable to detect that the lid is closed based upon a light sensor of the laptop device.

6. The contamination control system of claim 3, wherein the detection module is operable to detect that the lid is closed based upon a sleep state of the laptop device.

7. The contamination control system of claim 2, wherein: the electronic device comprises a tablet device; and the second event includes turning the tablet device face down.

8. The contamination control system of claim 1, wherein: the touch-based surface comprises a touch surface of the LCD touch panel and a keyboard separate from the LCD touch panel; the second event includes a detection that there is no motion in front of the electronic device; and decontaminating the touch-based surface comprises decontaminating the touch surface and the keyboard.

9. A method of decontaminating a touch-based surface of an electronic device, the method comprising:
 detecting, at a detection module of the electronic device, a first event indicating that a user has provided a touch-based input to the touch-based surface;
 sending, to a control module of the electronic device, a first indication based upon the first event;
 detecting a second event indicating that the user has moved away from the touch-based surface;
 sending a second indication based upon the second event;
 detecting a duration for the first event;
 sending a third indication when the duration for the first event exceeds a threshold;

determining that it is safe to turn on the UV light source to decontaminate the touch-based surface in response to the first indication, the second indication, and the third indication; and turning on an ultraviolet (UV) light source operable to shine on the touch-based surface in response to determining that it is safe to turn on the UV light source, wherein the UV light source comprises a UV light emitting diode (LED) configured within a raised profile of a case of the electronic device.

10. The method of claim 9, wherein:
the UV light source comprises a liquid crystal display (LCD) touch panel.

11. The method of claim 10, wherein:
the electronic device comprises a laptop computer;
the touch-based surface comprises a touch surface of the LCD touch panel and a keyboard;
the second event includes closing a lid of the laptop computer; and
decontaminating the touch-based surface comprises decontaminating the touch surface and the keyboard.

12. The method of claim 10, wherein;
the electronic device comprises a tablet device; and
the second event includes turning the tablet device face down.

13. The method of claim 9, wherein:
the UV light source comprises a UV light emitting diode (LED) configured within a case of the electronic device, the LED being disposed to shine on the touch-based surface.

14. The method of claim 13, wherein the LED is disposed within a bezel of the case.

15. A non-transitory computer-readable medium including code for performing a method, the method comprising:

detecting, at a detection module of an electronic device, a first event indicating that a user has provided a touch-based input to a touch-based surface;

sending, to a control module of the electronic device, a first indication based upon the first event;

detecting a second event indicating that the user has moved away from the touch-based surface;

sending a second indication based upon the second event;

detecting a duration for the first event;

sending a third indication when the duration for the first event exceeds a threshold;

determining that it is safe to turn on the UV light source to decontaminate the touch-based surface in response to the first indication, the second indication and the third indication; and turning on an ultraviolet (UV) light source operable to shine on the touch-based surface in response to determining that it is safe to turn on the UV light source, wherein the UV light source comprises a UV light emitting diode (LED) configured within a raised profile of a case of the electronic device.

\* \* \* \* \*